United States Patent
Sayama et al.

(10) Patent No.: US 6,575,938 B2
(45) Date of Patent: Jun. 10, 2003

(54) SYRINGE

(75) Inventors: Hideto Sayama, Kanagawa (JP); Shinji Yoshizawa, Kanagawa (JP)

(73) Assignee: Hori Glass Co., Ltd., Kanagawa (JP)

( * ) Notice: Subject to any disclaimer, the term of this patent is extended or adjusted under 35 U.S.C. 154(b) by 100 days.

(21) Appl. No.: 09/799,352

(22) Filed: Mar. 6, 2001

(65) Prior Publication Data

US 2001/0056264 A1 Dec. 27, 2001

(30) Foreign Application Priority Data

Jun. 21, 2000 (JP) .................................... 2000-185644

(51) Int. Cl.$^7$ .......................... A61M 5/00; A61M 5/315
(52) U.S. Cl. ........................ 604/181; 604/218; 604/228
(58) Field of Search ........................... 604/181, 187, 604/213, 218, 220, 222, 228, 227, 235; 222/386

(56) References Cited

U.S. PATENT DOCUMENTS

| | | | | |
|---|---|---|---|---|
| 3,930,492 A | * | 1/1976 | Hatsuno et al. | 600/577 |
| 4,367,738 A | * | 1/1983 | Legendre et al. | 604/110 |
| 4,994,034 A | * | 2/1991 | Botich et al. | 604/110 |
| 5,037,393 A | * | 8/1991 | Ellgass | 604/110 |

\* cited by examiner

Primary Examiner—Edward K. Look
Assistant Examiner—John K Fristoe, Jr.
(74) Attorney, Agent, or Firm—McDermott, Will & Emery

(57) ABSTRACT

Three collar groups 6A through 6C, each group comprising collars 5a through 5b, 5c through 5e and 5f through 5h which are thin walled and close to each other are provided in a spaced manner in a piston sliding direction. A first group 6A which is provided at the front most end of the piston head 5 comprises two collars 5a and 5b. The front collar 5a which is in contact with the liquid drug has a larger diameter than that of the rear collar 5b. First and third collar groups 6B and 6C which are at the rear of the first collar group 6A comprise three collars 5c to 5e and 5f to 5h, respectively. The intermediate collars 5d and 5g have larger diameters than those of the front and rear collars 5c and 5e; and 5f and 5h, respectively. A support collar 5i is provided at the rear of the collar groups 6B and 6C in such a manner that it is spaced therefrom. The support collar 5i has a thick walled portion x at its base excepting the peripheral edge thereof.

8 Claims, 3 Drawing Sheets

SYRINGE

BACKGROUND OF THE INVENTION

1. Field of the Invention

The present invention relates to a syringe and in particular to a syringe having a piston head which is made of a resin.

2. Related Art

As is well known, prior art syringe mainly comprises a cylinder which accommodates liquid such as drug and a piston which is reciprocally disposed within the cylinder. The piston comprises a piston main body and a piston head (gasket) which is secured to a front end of the piston main body by means of screwing and the like so that it slides along the inner wall of the cylinder while keeping the sealing condition therewith.

Recently, it is known that the cylinder is preferably made of any of cycloolefin resins in view of chemical resistance and heat resistance. On the other hand, the piston head is made of an elastomer such as butyl rubber since it should slide on and along the inner wall of the cylinder while keeping the liquid-tightness therewith.

However, such an elastomer requires a complicated and tedious washing step since plasticizers, cross-linking agents and pigments which are used with the elastomer may be dissolved to the chemical which is contained in the cylinder.

The elastomer (particularly, butyl rubber) has a low sliding ability for the inner surface of the cylinder. In order to make the reciprocal movement of the piston smoother, the inner face of the cylinder is coated with a lubricating agent such as silicone oil.

There is also a problem that it is hard to provide a high stability in size for the reason of the manufacturing process when the piston head is made of an elastomer.

Therefore, it is a main object of the present invention to achieve the simplification of the manufacturing process by omitting the washing step while satisfying the characteristics which are basically required for the syringe, to enable smooth sliding without using any lubricant, to enhance the dimension accuracy and stability and to achieve the reduction in cost by achieving the foregoing.

In view of the above-mentioned object, the present inventors have believed that the piston head is also made of a resin similarly to the cylinder to omit the washing step and to enhance the dimension accuracy and stability and have made efforts to study the manufacturing of the syringe. We have found from our study that if the prior art piston head is made of only a resin, there occur problems in liquid-tightness, sliding characteristics and ability of incorporation of the piston head into the cylinder. We have further made efforts on the research and development of the syringe to solve these latter problems together and made the present invention.

SUMMARY OF THE INVENTION

One embodiment of the invention resides in a syringe comprising a cylinder for containing liquid therein and a piston which is reciprocally disposed within the cylinder. The piston including a piston main body and a piston head made of a resin which is secured to a front end of the piston main body and slides along the inner wall of the cylinder while keeping the liquid-tightness therewith. The piston head is formed on the periphery thereof with collar means which contacts with the inner wall of the cylinder, at least the peripheral edge of the collar means being thin walled. The collar means being slidable on and along the inner wall of the cylinder while keeping the liquid-tightness.

An aspect of the invention resides in the collar means comprises collars which are spaced in a direction of sliding of the piston. The collar of at least two adjacent collars, which is on the front side in the sliding direction being supported by the collar which is in the rear side in the sliding direction when the piston slides.

Another aspect of the invention resides in the syringe having a collar means having a base end portion which is thick walled excepting for the peripheral edge.

Another embodiment of the invention resides in a syringe comprising a cylinder for containing liquid therein and a piston which is reciprocally disposed within the cylinder. The piston including a piston main body and a piston head made of a resin which is secured to a front end of the piston main body and slides along the inner wall of the cylinder while keeping the liquid-tightness therewith. The piston head is formed on the periphery thereof with collar groups, each comprising two collars which are close to each other, at least the peripheral edge of each of the collars being thin walled. The collars being slidable on and along the inner wall of the cylinder while keeping the liquid-tightness. The front collar of the collar group having a diameter which is larger than that of the rear collar. The front collar having a larger diameter being supported by the rear collar when the piston is inserted into the cylinder.

Still another embodiment of the invention resides in a syringe comprising a cylinder for containing liquid therein and a piston which is reciprocally disposed within the cylinder. The piston including a piston main body and a piston head made of a resin which is secured to a front end of the piston main body and slides along the inner wall of the cylinder while keeping the liquid-tightness therewith. The piston head is formed on the periphery thereof with collar groups, each comprising three collars which are close to each other, at least the peripheral edge of each of the collars being thin walled. The collars being slidable on and along the inner wall of the cylinder while keeping the liquid-tightness. The intermediate collar of the collar group having a diameter which is larger than that of the front and rear collars. The intermediate collar having a larger diameter being supported by the front and rear collars when the piston is slided in the cylinder.

Yet another embodiment of the invention resides in a syringe comprising a cylinder for containing liquid therein and a piston which is reciprocally disposed within the cylinder. The piston including a piston main body and a piston head made of a resin which is secured to a front end of the piston main body and slides along the inner wall of the cylinder while keeping the liquid-tightness therewith. The piston head is formed on the periphery thereof with at least two collar groups being spaced in a direction of sliding of the piston, each group comprising collars which are close to each other, at least the peripheral edge of each of the collars being thin walled. The collars being slidable on and along the inner wall of the cylinder while keeping the liquid-tightness. The collar group at the distal end comprises two collars. The front collar of the frontmost collar group having a diameter which is larger than that of the rear collar. The front collar having a larger diameter being supported by the rear collar when the piston is inserted into the cylinder. The collar group which is at the rear of the frontmost collar group comprises three collars, the intermediate collar having a diameter which is larger than those of the front and rear collars. The intermediate collar having a larger diameter being supported by the front or rear collar at least when the piston slides, wherein a piston support collar which is thick walled at the base end thereof excepting for the peripheral edge thereof is provided at the rear of these collar groups in a spaced relationship therewith.

An aspect of the invention resides the piston head being formed of a resin which is selected from the group consisting of polypropylene, polyethylene, fluorine, cyclopolyolefin, and polycarbonate resins.

DESCRIPTION OF MODES OF EMBODYING THE INVENTION

Now, the present invention will be described in more detail with reference to a mode of embodying the invention which is illustrated in the annexed drawings. FIG. 1 shows the mode of embodying a syringe of the present invention. The syringe 1 comprises a cylinder 2 which accommodates some liquid such as pharmaceutical drug and a piston 3 which is reciprocally disposed within the cylinder 2. The piston 3 comprises a piston main body 4 and a piston head 5 made of a synthetic resin, which is secured to a front end of the piston main body 4 by means of screwing and the like and is slidable on and along the inner wall of the cylinder 2 while keeping the liquid-tightness therewith. Specifically, the piston head 5 is formed on its periphery with collars 5a through 5i which are in contact with the inner wall of the cylinder as shown in FIG. 2. The collars 5a through 5i are thin-walled at least at the peripheral edges thereof (the whole of the collars in the illustrated case). Although the thickness of the thin walled collars cannot be specified since the flexure of the collars should be provided depending upon the hardness of the material, it is preferably 0.1 to 0.5 mm, more preferably 0.2 to 0.4 mm. In case in which the collars 5a to 5i are thin walled at least at the peripheral edge thereof in such a manner, low contact resistance is necessary since the contact area between the collars 5a to 5i and the inner face of the cylinder 2 is small, resulting in that the piston 3 can be smoothly slid without using any lubricant such as silicone oil. It is necessary to make the outer diameter of the collars 5a to 5i slightly (about 0.05 to 0.06 mm) larger than the inner diameter of the cylinder 2 in such a manner that the collars 5a through 5i are in an intimate contact with the cylinder 2. The collars 5a through 5i are slightly contractible in a radial direction due to the characteristics of its material and they are received within the cylinder 2 in a more or less flexed manner due to small thickness, which will not prevent its sliding movement.

The fact that such plural collars 5a through 5i are provided in a spaced manner in a piston-sliding direction as illustrated in the drawing does not only achieve prevention of liquid-leakage with multi-seal, but also constantly keeps the piston 3 in a parallel relationship with the piston sliding direction.

The material which may be used to form the piston head 5 may include polypropylene, polyethylene, fluorine, cyclopolyolefin and polycarbonate resins, which are selected from the resins preferable for medical instruments. Particularly, cyclopolyolefin resins are preferable in view of chemical resistance, heat resistance and transparency. Making the piston head 5 of a synthetic resin reduces the amount of materials which are dissolved to drugs so that the washing step can be eliminated. Known molding process can be adopted and the dimensional accuracy and stability of the molded syringe becomes higher.

In present embodiment, plural collars 5a through 5i are not only provided in a spaced manner in a piston sliding direction (of course, they may be provided in such a manner). Three collar groups 6A through 6C, each group comprising plural collars 5a through 5b, 5c through 5e and 5f through 5h respectively which are thin walled and close to each other are provided in a spaced manner in a piston sliding direction. A first group 6A which is provided at the frontmost end of the piston head 5 comprises two collars 5a and 5b. The front collar 5a which is in contact with the liquid drug has a larger diameter than that of the rear collar 5b. First and third collar groups 6B and 6C which are at the rear of the first collar group 6A comprise three collars 5c to 5e and 5f to 5h, respectively. The intermediate collars 5d and 5g have larger diameters than those of the front and rear collars 5c and 5e; and 5f and 5h, respectively. A support collar 5i is provided at the rear of the collar groups 6B and 6C in such a manner that it is spaced therefrom. The support collar 5i has a thick walled portion x at its base excepting the peripheral edge thereof.

Specifically, the space between the collars of each collar group 6A to 6C is in the order of about the thickness of the collar. The space between the collar groups is about 2.2 to 2.3 mm. The rear collar 5b of the first collar group 6A has a diameter which is about 0.05 mm larger than the inner diameter of the cylinder. The front collar 5a has a diameter which is larger by about 0.1 mm than that of the rear collar 5b. The front and rear collars 5c. 5e. 5f and 5h of the second and third collar groups 6b and 6c have a diameter which is larger by about 0.05 mm than the inner diameter of the cylinder. The intermediate collars 5d and 5g have a diameter which is larger by about 0.1 mm than that of the front and rear collars. The outer diameter of the piston support collar 5i is equal to those of the larger collars 5a, 5d and 5g of the first to third collar groups, respectively.

When the piston 3 is depressed into the thus formed syringe 1, the larger diameter front collar 5a of the first collar group 6A flexes in such a manner that it is slightly tilted rearwardly as shown in FIG. 3. However, it is hard for the peripheral edge of the front collar 5a to separate from the inner face of the cylinder 2 since the rearwardly tilted front collar is supported by the rear collar 5b. Accordingly, the liquid drug is hardly leaked from the interface between the cylinder and the outer peripheral edge of the collar 5a so that it is possible to positively expel the liquid drug. Although, similarly the intermediate collars 5d and 5g of the second and third collar groups of the second and third collar groups 6B and 6C, respectively flex in such a manner that they are slightly tilted rearwardly, the rearwardly tilted intermediate collars 5d and 5g are supported by the rear collars 5e and 5h, respectively. Accordingly, a close contact between the second and third collar groups 6B and 6C and the inner face of the cylinder 2 is assured. If the liquid drug should be leaked from the first collar group 6A, the leaked liquid can not only be blocked by the rear second and third collar groups 6B and 6C, but also the parallel relationship between the piston 3 and the piston sliding direction can be constantly maintained.

The piston 3 may be pulled for confirming the puncture position after a syringe needle is inserted into a patient for injection. At this time, although the intermediate collars 5d and 5g having a larger diameter of the second and third collar groups 6B and 6C, respectively flex in such a manner that they are slightly tilted forwardly as shown in FIG. 4, the forwardly tilted intermediate collars 5d and 5g are supported by the front collars 5c and 5e. A close contact between the second and third collar groups 6B and 6C and the inner face of the cylinder 2 is assured. Although no collar supports the front collar 6a of the first collar group 6A when the piston 3 is pulled, the liquid drug is hardly leaked since a negative pressure is generated in a drug holding area in the cylinder 2 even if the front collar 6a in interest should flex more or less forwardly.

On the other hand, the piston support collar 5i performs a function to prevent the piston 3 which is constantly kept in a parallel relationship with the sliding direction from being tilted as well as a liquid leakage preventing function. It is harder for the peripheral edge Y of the collar 5h to be tilted than the other thin walled collars 5a to 5h due to the presence of the thick walled base X. The piston support collar 5i more effectively performs a function to prevent the piston 3 from being tilted particularly when the syringe is plugged.

In other words, it has been known that the process for manufacturing a syringe 1 having the cylinder 2 which has been preliminarily filled with the liquid drug comprises the steps of loading the liquid drug into the cylinder 2 through an opening at the base thereof while the discharge exit 2A at the tip end of the cylinder 2A is clogged with the plug Z1 adapting the piston 3 into the opening 2b at the base end of the cylinder after evacuating the space within the cylinder and moving the piston 3 to a given position within the cylinder 2 by a negative pressure therein by returning the pressure outside of the cylinder to a normal pressure.

In this case, smooth insertion of the piston 3 may be prevented by the tilting of the portion of the piston 2 at the base end then the insertion is conducted.

In contrast to this, presence of the above-mentioned piston support collar 5i which is hard to tilt enables the portion of the piston at the base end to be positively supported centrally of the cylinder 2, which leads to smooth and positive plugging.

Other Features (a) The first collar group 6A in the foregoing embodiment may comprise three collars having a larger diameter including an intermediate collar similarly to the second and third collar groups 6b and 6c (not shown). However, in this case, the drug liquid is liable to leak into the space between the front collar and the intermediate collar of the first collar group when the piston 3 is adapted into the cylinder. Therefore, the arrangement of the first collar group in the foregoing embodiment is more preferable.

(b) Conversely, the second and third collar groups b and 6c may comprise two collars including a front collar having a larger diameter similarly to the first collar group 6A.

(c) In accordance with the present invention, the piston support collars 5i in the foregoing embodiment maybe provided in a longitudinal direction of the piston. Only the piston support collars 5i having a thin wall at the periphery thereof and a thick wall at the base end thereof may be provided in a longitudinal direction of the piston.

(d) Although the syringe of the present invention is preferable for liquid drugs (or medical liquid), it may be used for accommodating and expelling the other liquids.

As mentioned above, in accordance with the present invention, simplification of the manufacturing process can be achieved by eliminating the washing step while satisfying the characteristics which are basically required for the syringe, smooth sliding of the piston is made possible without using any lubricant, the accuracy of size and stability can be enhanced so that reduction in cost can be achieved.

Figure 1:
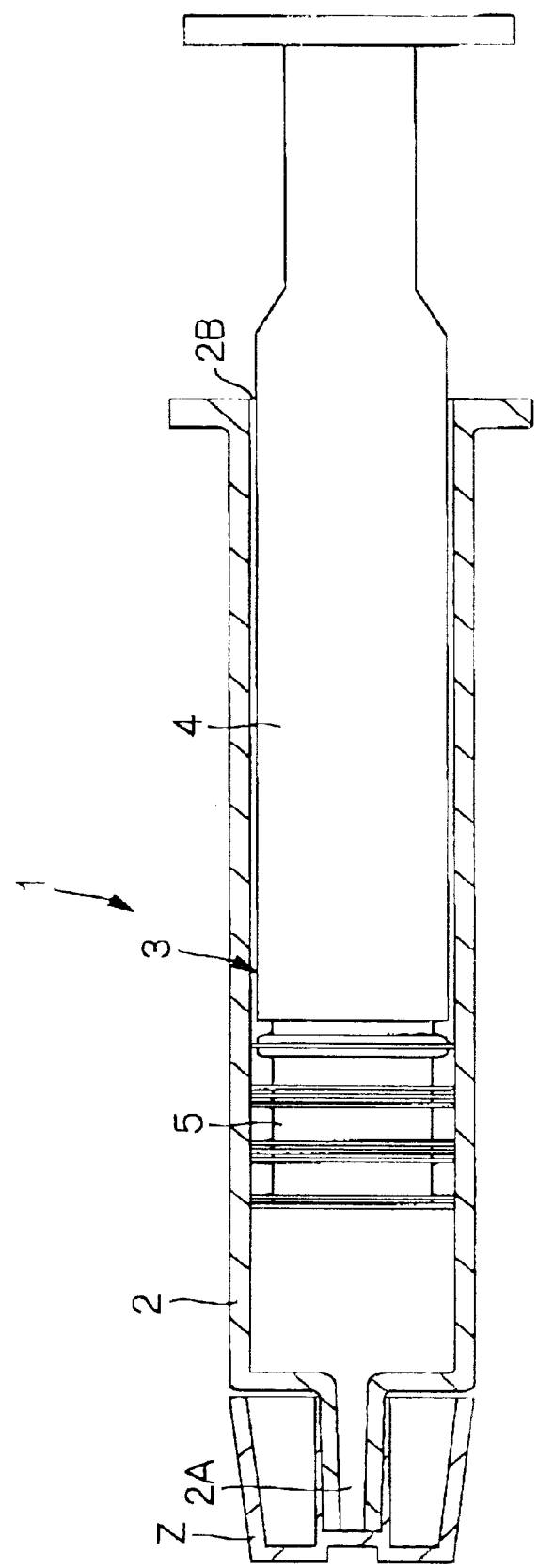
FIG. 1 is a longitudinal sectional view showing the syringe of the present invention.
Figure 2:
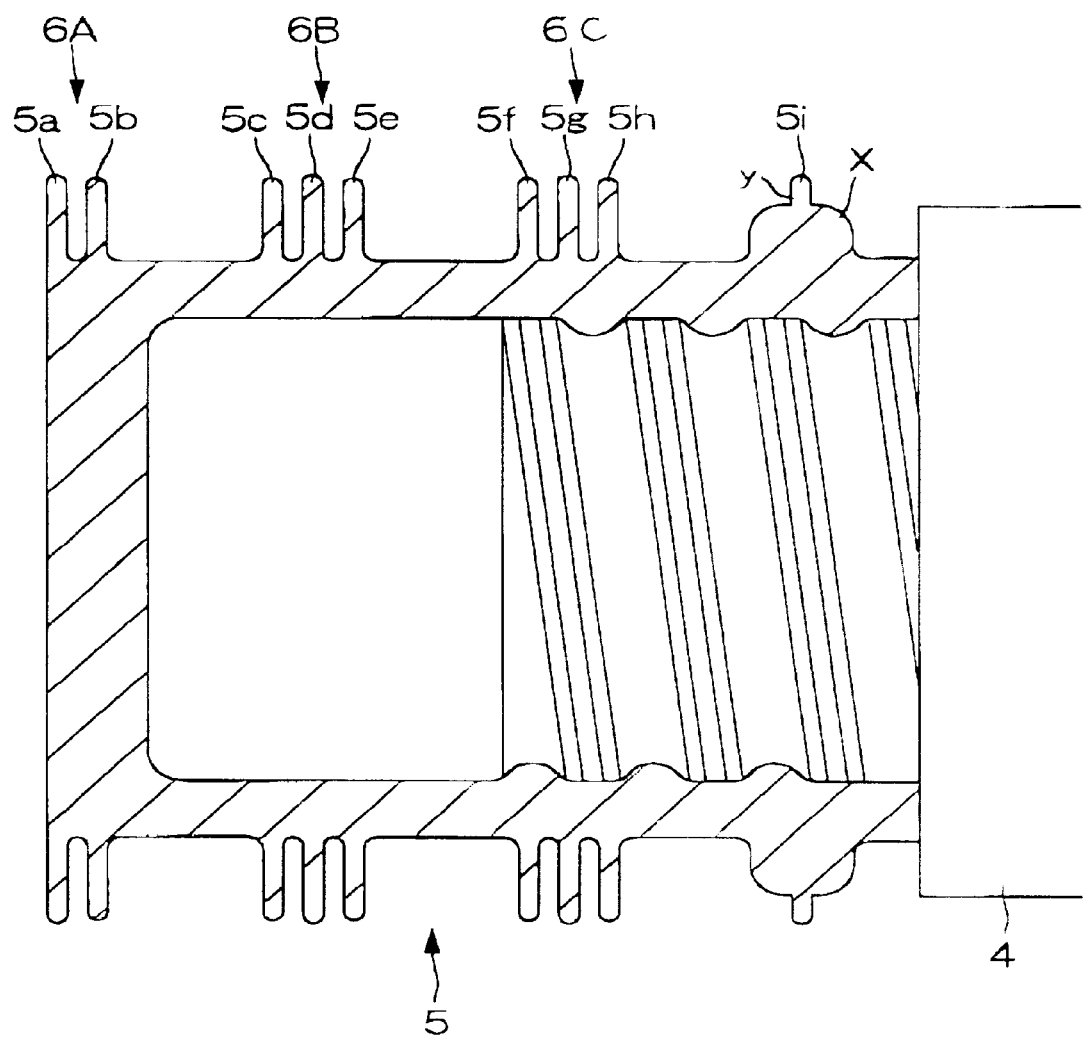
FIG. 2 is a longitudinal sectional view showing a main part of the piston of the present invention.
Figure 3:
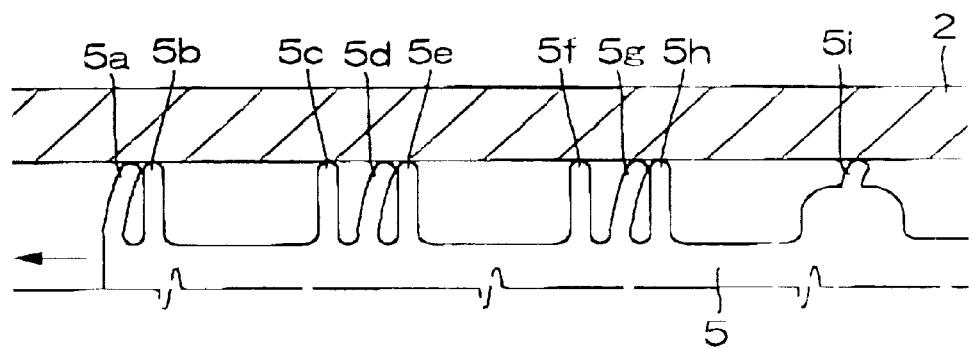
FIG. 3 is a longitudinal sectional view showing a condition when the piston is inserted.
Figure 4:
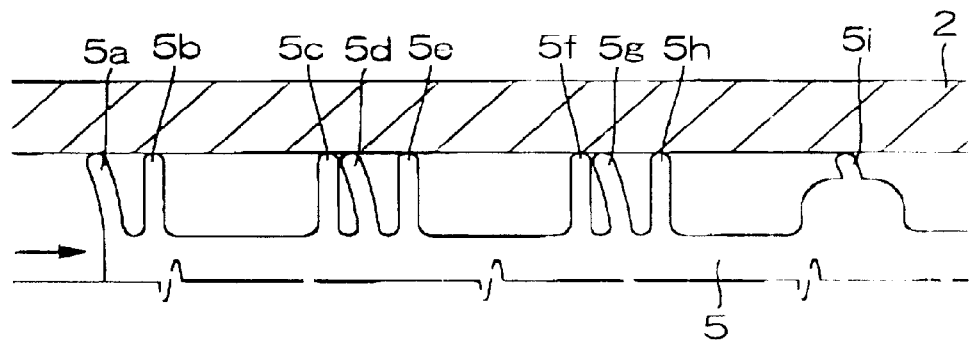
FIG. 4 is a longitudinal sectional view showing a condition when the piston is pulled.

What is claimed is:

1. A syringe comprising a cylinder for containing liquid therein and a piston which is reciprocally disposed within said cylinder, said piston including a piston main body and a piston head made of a resin which is secured to a front end of the piston main body and slides along the inner wall of said cylinder while keeping the liquid-tightness therewith, wherein said piston head is formed on the periphery thereof with collar means which contacts with the inner wall of the cylinder, at least the peripheral edge of said collar means being thin walled, said collar means being slidable on and along the inner wall of said cylinder while keeping the liquid-tightness, and said collar means comprises collars which are spaced in a direction of sliding of said piston, a first collar adjacent a second collar, said first collar positioned on a front side in the sliding direction, and said second collar positioned on a rear side in the sliding direction, and said first collar being supported by said second collar when said piston slides.

2. A syringe as defined in claim 1 in which said syringe has collar means having a base end portion which is thick walled excepting for said peripheral edge.

3. A syringe as defined in claim 1 in which said piston head is formed of a resin which is selected from the group consisting of polypropylene, polyethylene, fluorine, cyclopolyolefin, and polycarbonate resins.

4. A syringe as defined in claim 1, wherein the thickness of the thin wall is less than 0.5 mm.

5. A syringe as defined in claim 1, wherein a distance between adjacent collars in a collar group is less than 0.5 mm.

6. A syringe comprising a cylinder for containing liquid therein and a piston which is reciprocally disposed within said cylinder, said piston including a piston main body and a piston head made of a resin which is secured to a front end of the piston main body and slides along the inner wall of said cylinder while keeping the liquid-tightness therewith, wherein said piston head is formed on the periphery thereof with collar groups, each comprising two collars which are close to each other, at least the peripheral edge of each of said collars being thin walled, said collars being slidable on and along the inner wall of said cylinder while keeping the liquid-tightness, the front collar of said collar group having a diameter which is larger than that of the rear collar, said front collar having a larger diameter being supported by the rear collar when said piston is inserted into the cylinder.

7. A syringe comprising a cylinder for containing liquid therein and a piston which is reciprocally disposed within said cylinder, said piston including a piston main body and a piston head made of a resin which is secured to a front end of the piston main body and slides along the inner wall of said cylinder while keeping the liquid-tightness therewith, wherein said piston head is formed on the periphery thereof with collar groups, each comprising three collars which are close to each other, at least the peripheral edge of each of said collars being thin walled, said collars being slidable on and along the inner wall of said cylinder while keeping the liquid-tightness, the intermediate collar of said collar group having a diameter which is larger than that of the front and rear collars, said intermediate collar having a larger diameter being supported by the front and rear collars when said piston is slided in the cylinder.

8. A syringe comprising a cylinder for containing liquid therein and a piston which is reciprocally disposed within said cylinder, said piston including a piston main body and a piston head made of a resin which is secured to a front end of the piston main body and slides along the inner wall of said cylinder while keeping the liquid-tightness therewith, wherein said piston head is formed on the periphery thereof with at least two collar groups being spaced in a direction of sliding of the piston, each group comprising collars which are close to each other, at least the peripheral edge of each of said collars being thin walled, said collars being slidable on and along the inner wall of said cylinder while keeping the liquid-tightness, wherein the frontmost collar group comprises two collars, the front collar of said frontmost collar group having a diameter which is larger than that of the rear collar, said front collar having a larger diameter being supported by the rear collar when said piston is inserted into the cylinder, wherein the collar group which is at the rear of said frontmost collar group comprises three collars, the intermediate collar having a diameter which is larger than those of the front and rear collars, the intermediate collar having a larger diameter being supported by the front or rear collar at least when said piston slides, wherein a piston support collar which is thick walled at the base end thereof excepting for the peripheral edge thereof is provided at the rear of these collar groups in a spaced relationship therewith.

* * * * *